United States Patent
Nishioka et al.

(10) Patent No.: US 8,695,399 B2
(45) Date of Patent: Apr. 15, 2014

(54) DETECTOR FOR DETECTING SULFUR COMPONENTS

(75) Inventors: Hiromasa Nishioka, Susono (JP); Yoshihisa Tsukamoto, Susono (JP); Katsuhiko Oshikawa, Tokyo (JP); Hiroshi Otsuki, Susono (JP); Junichi Matsuo, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 5 days.

(21) Appl. No.: 13/255,009

(22) PCT Filed: Dec. 9, 2009

(86) PCT No.: PCT/JP2009/070934
§ 371 (c)(1),
(2), (4) Date: Sep. 6, 2011

(87) PCT Pub. No.: WO2011/070687
PCT Pub. Date: Jun. 16, 2011

(65) Prior Publication Data
US 2012/0279278 A1 Nov. 8, 2012

(51) Int. Cl.
*G01N 7/00* (2006.01)
(52) U.S. Cl.
USPC ........................................................ 73/23.31
(58) Field of Classification Search
USPC ........................................................ 73/23.31
See application file for complete search history.

(56) References Cited

U.S. PATENT DOCUMENTS

| 4,186,176 A * | 1/1980 | Kitamura et al. ............. 423/235 |
| 6,274,106 B1 * | 8/2001 | Held ........................... 423/213.2 |
| 2004/0041879 A1 | 3/2004 | Sakamoto et al. |

FOREIGN PATENT DOCUMENTS

| JP | A-2004-92431 | 3/2004 |
| WO | WO 2008/088072 A1 | 7/2008 |

OTHER PUBLICATIONS

Jun. 12, 2012 International Preliminary Report on Patentability issued in International Patent Application No. PCT/JP2009/070934 (with translation).
International Search Report mailed Mar. 16, 2010 issued in International Patent Application No. PCT/JP2009/070934 (with translation).

* cited by examiner

*Primary Examiner* — R. A. Smith
*Assistant Examiner* — Alex Devito
(74) *Attorney, Agent, or Firm* — Oliff PLC

(57) ABSTRACT

The present detector for detecting sulfur components includes a storage portion for storing SOx and NOx in the exhaust gas passing through an exhaust passage, in which the more an amount of stored SOx increases, the more an amount of NOx that can be stored decreases, estimates the amount of stored SOx on the basis of an amount of NOx stored in the storage portion, and detects an integrated amount of SOx passing through the exhaust passage during a given period or an value on the basis of the integrated amount. In the present detector, the estimating of the amount of stored SOx for detecting the integrated amount of SOx or the value on the basis of the integrated amount is prohibited when a current amount of NOx that can be stored is not stored in the storage portion.

8 Claims, 4 Drawing Sheets

EXHAUST GAS FLOW →

EXHAUST GAS FLOW →

DETECTOR FOR DETECTING SULFUR COMPONENTS

TECHNICAL FIELD

The present invention relates to a detector for detecting sulfur components.

BACKGROUND ART

A $SO_x$ concentration sensor for detecting a $SO_x$ concentration in the exhaust gas is known. A usual $SO_x$ concentration sensor measures an electromotive force produced when $SO_x$ changes into sulfuric acid ion within solid electrolyte, to detect a $SO_x$ concentration in the exhaust gas. However, it is difficult for such a $SO_x$ concentration sensor for detecting an instantaneous $SO_x$ concentration to detect an accurate $SO_x$ concentration when the $SO_x$ concentration in the exhaust gas is low.

A proposed detector for detecting sulfur components cannot detect an instantaneous $SO_x$ concentration but can detect an integrated amount of $SO_x$ passing through the exhaust passage during a given period (for example, refer to Japanese Unexamined Patent Publication No. 2008-175623).

The detector for detecting sulfur components comprises a $SO_x$ storage portion for storing $SO_x$ contained in the exhaust gas, measures a property such as an electric resistance, an volume, a heat capacity or the like of the $SO_x$ storage portion changing with the increase of an amount of $SO_x$ stored in the $SO_x$ storage portion and detects an integrated amount of $SO_x$ passing through the exhaust passage during a given period on the basis of the measured property.

DISCLOSURE OF THE INVENTION

Because it is difficult to accurately measure a change of a property such as an electric resistance, a volume, a heat capacity or the like, the above-mentioned detector may be not able to accurately detect an integrated amount of $SO_x$ passing through the exhaust passage during a given period.

Accordingly, an object of the present invention is to provide a detector for detecting sulfur components, which can accurately measure an integrated amount of $SO_x$ passing through the exhaust passage in a given period or a value on the basis of the integrated amount.

A detector for detecting sulfur components according to a first aspect of the invention can include a storage portion for storing $SO_x$ and $NO_x$ in the exhaust gas passing through an exhaust passage, in which the more an amount of stored $SO_x$ increases, the more an amount of $NO_x$ that can be stored decreases, and an electronic control unit configured to (i) estimate the amount of stored $SO_x$ on the basis of an amount of $NO_x$ stored in the storage portion, and (ii) estimate an integrated amount of $SO_x$ passing through the exhaust passage during a given period or a value on the basis of the integrated amount. The electronic control unit (ECU) prohibits the estimating of the amount of stored $SO_x$ for estimating the integrated amount of $SO_x$ or the value on the basis of the integrated amount when a current amount of $NO_x$ that can be stored is not stored in the storage portion.

According to a second aspect, the detector also can include a temperature sensor that detects a temperature of the storage portion, and the ECU prohibits the estimating of the amount of stored $SO_x$ for estimating the integrated amount of $SO_x$ or the value on the basis of the integrated amount when the temperature of the storage portion is out of a set temperature range.

According to a third aspect, in the detector of the second aspect, the set temperature range includes a temperature at which a current amount of $NO_x$ that can be stored in the storage portion is maximized.

According to a fourth aspect of the detector, after all $NO_x$ and $SO_x$ stored in the storage portion are released, the ECU estimates an amount of $NO_x$ stored in the storage portion during a set period by releasing all the amount of stored $NO_x$, when the set period is gradually lengthened, each amount of $NO_x$ stored in the storage portion during each set period is estimated, and a maximum value of the estimated amounts of stored $NO_x$ is set as the current amount of $NO_x$ that can be stored in the storage portion when $SO_x$ is not stored.

A detector according to a fifth aspect of the present invention further includes an oxygen pump, wherein the storage portion stores $NO_x$ in the exhaust gas as nitrate and the oxygen pump supplies oxygen in the vicinity of the storage portion.

According to the detector of the first aspect of the present invention, the detector comprises a storage portion for storing $SO_x$ and $NO_x$ in the exhaust gas passing through an exhaust passage, in which the more an amount of stored $SO_x$ increases, the more an amount of $NO_x$ that can be stored decreases, the ECU estimates an amount of stored $SO_x$ on the basis of an amount of $NO_x$ stored in the storage portion, and the ECU estimates an integrated amount of $SO_x$ passing through the exhaust passage during a given period or an value on the basis of the integrated amount on the basis the amount of stored $SO_x$ in the storage portion because a given rate of an amount of $SO_x$ passing through the exhaust passage is stored in the storage portion of the detector. In the estimating of the amount of stored $SO_x$ for estimating the integrated amount of $SO_x$ or the value on the basis of the integrated amount, a current amount of $NO_x$ that can be stored must be stored in the storage portion. If the amount of stored $SO_x$ was estimated on the basis of the amount of stored $NO_x$ when the current amount of $NO_x$ that can be stored was not stored in the storage portion, the estimated amount of stored $SO_x$ will become more than the actual amount. Accordingly, the ECU prohibits the estimating of the amount of stored $SO_x$ for estimating the integrated amount of $SO_x$ or the value on the basis of the integrated amount when a current amount of $NO_x$ that can be stored is not stored in the storage portion.

According to the detector of the second aspect of the present invention, a temperature sensor detects a temperature of the storage portion, and the ECU prohibits the estimating of the amount of stored $SO_x$ for detecting estimating the integrated amount of $SO_x$ or the value on the basis of the integrated amount when the temperature of the storage portion is out of a set temperature range. Because a current amount of $NO_x$ that can be stored in the storage portion changes in accordance with a temperature of the storage portion, and if the amount of stored $SO_x$ was estimated on the basis of the amount stored $NO_x$ when the temperature of the storage portion became out of the set temperature range and the current amount of $NO_x$ that can be stored decreased (or increased) by the change of the temperature, the estimated amount of stored $SO_x$ will become more (or less) than the actual amount.

According to the detector of the third aspect of the present invention, the set temperature range includes a temperature at which a current amount of $NO_x$ that can be stored in the storage portion is maximized. Therefore, when the amount of stored $SO_x$ for estimating the integrated amount of $SO_x$ or the value on the basis of the integrated amount is estimated, the amount of stored $NO_x$ becomes relatively large so that the amount of stored $NO_x$ can be easily measured.

According to the detector of the fourth aspect of the present invention, after all $NO_x$ and $SO_x$ stored in the storage portion are released, the ECU estimates an amount of $NO_x$ stored in the storage portion during a set period by releasing all the amount of stored $NO_x$, when the set period is gradually lengthened, each amount of $NO_x$ stored in the storage portion during each set period is estimated, and a maximum value of the estimated amounts of stored $NO_x$ is set as the current amount of $NO_x$ that can be stored in the storage portion when $SO_x$ is not stored. The current amount of $NO_x$ that can be stored in the storage portion when $SO_x$ is not stored, changes in accordance with deterioration of the storage portion. Thus, when all $NO_x$ and $SO_x$ stored in the storage portion are released, the current amount of $NO_x$ that can be stored in the storage portion when $SO_x$ is not stored, can be reliably updated without $SO_x$ stored in the storage portion as the storage portion is not exposed in the exhaust gas for a long time. Therefore, when the amount of stored $SO_x$ for estimating the integrated amount of $SO_x$ or the value on the basis of the integrated amount is estimated, the amount of stored $SO_x$ can be estimated relative accurately on the basis of the amount of $NO_x$ stored in the storage portion.

According to the detector of the fifth aspect of the present invention, the storage portion stores $NO_x$ in the exhaust gas as nitrate so that when an oxygen pump supplies oxygen in the vicinity of the storage portion, NO in the exhaust gas is oxidized to $NO_2$ by the supplied oxygen so as to be easily stored in the storage portion as nitrate.

BEST MODE FOR CARRYING OUT THE INVENTION

Figure 1:
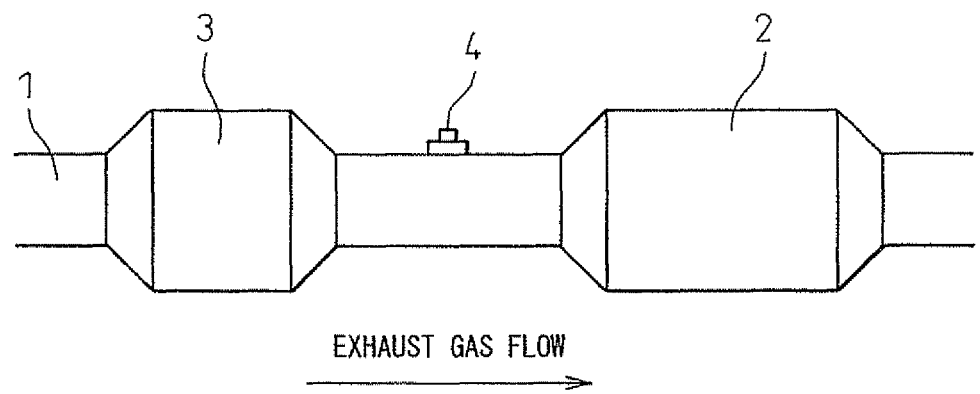
FIG. 1 is a schematic view showing an engine exhaust system in which a detector for detecting sulfur components according to the present invention is arranged.

FIG. 1 is a schematic view showing an engine exhaust system in which a detector for detecting sulfur components according to the present invention is arranged. In FIG. 1, reference numeral 1 is an exhaust passage of an internal combustion engine. The engine performs lean combustion such as in a diesel engine or a direct fuel injection-type spark-ignition engine. The exhaust gas of such an engine includes a relatively large amount of $NO_x$ so that a $NO_x$ catalyst device 2 for purifying $NO_x$ is arranged in the exhaust passage 1.

The $NO_x$ catalyst device 2 carries a $NO_x$ storage material and a noble metal catalyst such as platinum Pt. The $NO_x$ storage material is at least one element selected from for example potassium K, sodium Na, lithium Li, cesium Cs, or another alkali metal, barium Ba, calcium Ca, or another alkali earth metal, and lanthanum La, yttrium Y, or another rare earth.

The $NO_x$ catalyst device 2 satisfactorily stores NO in the exhaust gas so as to absorb $NO_x$ as nitrate or so as to adsorb $NO_x$ as $NO_2$ when the air-fuel ratio of the exhaust gas is lean, that is, when the oxygen concentration of the exhaust gas is high. However, the $NO_x$ catalyst device cannot store $NO_x$ without limitation. Accordingly, before the $NO_x$ catalyst device can not almost store further $NO_x$ because an amount of $NO_x$ stored in the $NO_x$ catalyst device almost reaches the largest amount of $NO_x$ that can be stored therein, the air-fuel ratio of the exhaust gas is changed to a stoichiometric air-fuel ratio or a rich air-fuel ratio as the regeneration treatment, namely, the concentration of oxygen of the exhaust gas is lowered. Therefore, the stored $NO_x$ is separated, namely, the absorbed $NO_x$ is released or the adsorbed $NO_2$ is disconnected, and thereafter the separated $NO_x$ is reduced and purified to $N_2$ by reducing materials in the exhaust gas.

Once the $NO_x$ catalyst device 2 stores $SO_x$ in the exhaust gas as sulfate, sulfate is more stable than nitrate so that the stored $SO_x$ cannot be released by the regeneration treatment and an amount of $NO_x$ that can be stored drops (sulfur contamination). Therefore, a S trap device 3 which can store $SO_x$ in the exhaust gas is arranged upstream of the $NO_x$ catalyst device 2 in the exhaust passage 1 to restrain the sulfur contamination of the $NO_x$ catalyst device 2.

The detector for detecting sulfur components 4 according to the present invention is arranged, for example, between the S trap device 3 and the $NO_x$ catalyst device 2, and detects an integrated amount of $SO_x$ passing through the S trap device 3. When the integrated amount of $SO_x$ reaches a set value, it can be determined that it is a time to exchange the S trap device 3 for a new one.

Figure 2:
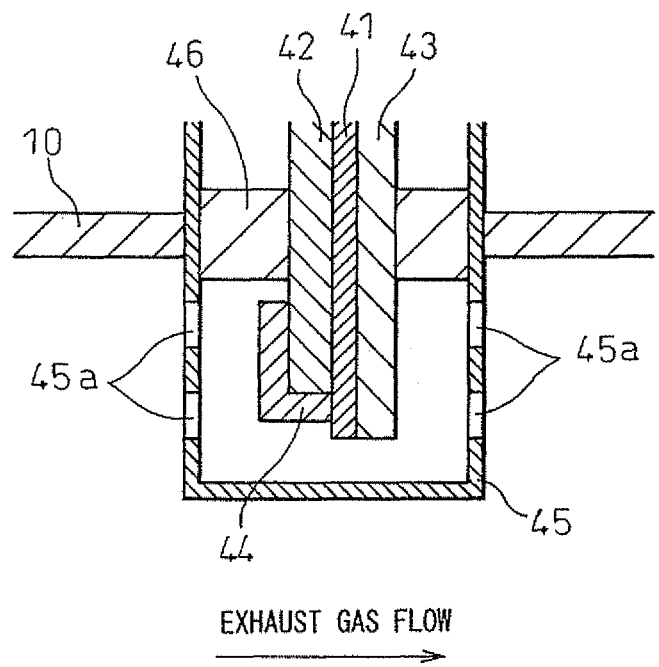
FIG. 2 is a schematic sectional view showing an embodiment of the detector for detecting sulfur components according to the present invention.

FIG. 2 is a schematic sectional view showing an embodiment of the detector for detecting sulfur components 4 according to the present invention. In FIG. 2, reference numeral 10 is an outer wall of the exhaust passage 1. Reference numeral 41 is a base plate of the detector for detecting sulfur components 4. A temperature sensor 42 such as a thermocouple is arranged on one side (preferably exhaust gas upstream side) of the base plate 41. On the other hand, an electric heater 43 is arranged on the other side of the base plate 41. Reference numeral 44 is a storage portion for $NO_x$ and $SO_x$ arranged so as to cover the temperature sensitive portion of the temperature sensor 42. Reference numeral 45 is a cylindrical case which surrounds the detector for detecting sulfur components 4 having the above-construction and goes through the outer wall 10 of the exhaust passage 1.

A plurality of openings 45a is formed on the case 45. The exhaust gas passing through the exhaust passage 1 flows into the case 45 via the openings 45a. Reference numeral 46 is an oxygen pump for supplying oxygen (for example, oxygen in the atmosphere) in the vicinity of the storage portion 44 within the case 45, and the oxygen pump is arranged around the unit of the temperature sensor 42, the base plate 41, and the electric heater 43 to separate the space around the storage portion 44 within the case 45 from the atmosphere chamber. The oxygen pump 46 is made from zirconia or the like. In contrast with a zirconia oxygen sensor, the oxygen pump can make oxygen in the atmosphere move to the vicinity of the storage portion 44 within the case 45 by impressing voltage.

The storage portion 44 stores $NO_x$ and $SO_x$ in the exhaust gas and can be formed to apply the above-mentioned $NO_x$ storage material and a noble metal catalyst such as platinum Pt on the temperature sensitive portion of the temperature sensor 42.

As mentioned above, the storage portion 44 constructed like this absorb $NO_x$ in the exhaust gas as nitrate and absorb $SO_x$ in the exhaust gas as sulfate instead of $NO_x$. The storage portion 44 has an amount of $NO_x$ that can be stored (B) when $SO_x$ is not stored (or an amount of $NO_x$ and $SO_x$ that can be stored). Sulfate is more stable than nitrate so that an amount of $NO_x$ that can be stored (B) when $SO_x$ is not stored is a standard and the more an amount of stored $SO_x$ increases, the more a current amount of $NO_x$ that can be stored decrease.

On the basis of this relationship, an integrated amount of $SO_x$ passing through the exhaust passage 1 at the position of the detector for detecting sulfur components during a given period can be detected, or an average value of each $SO_x$ concentration in the exhaust gas passing through the exhaust passage 1 at the position of the detector for detecting sulfur components during the given period or an average value of each amount of $SO_x$ passing through the exhaust passage 1 at the position of the detector for detecting sulfur components during the given period can be detected as a value on the basis of the integrated amount of $SO_x$.

Figure 3:
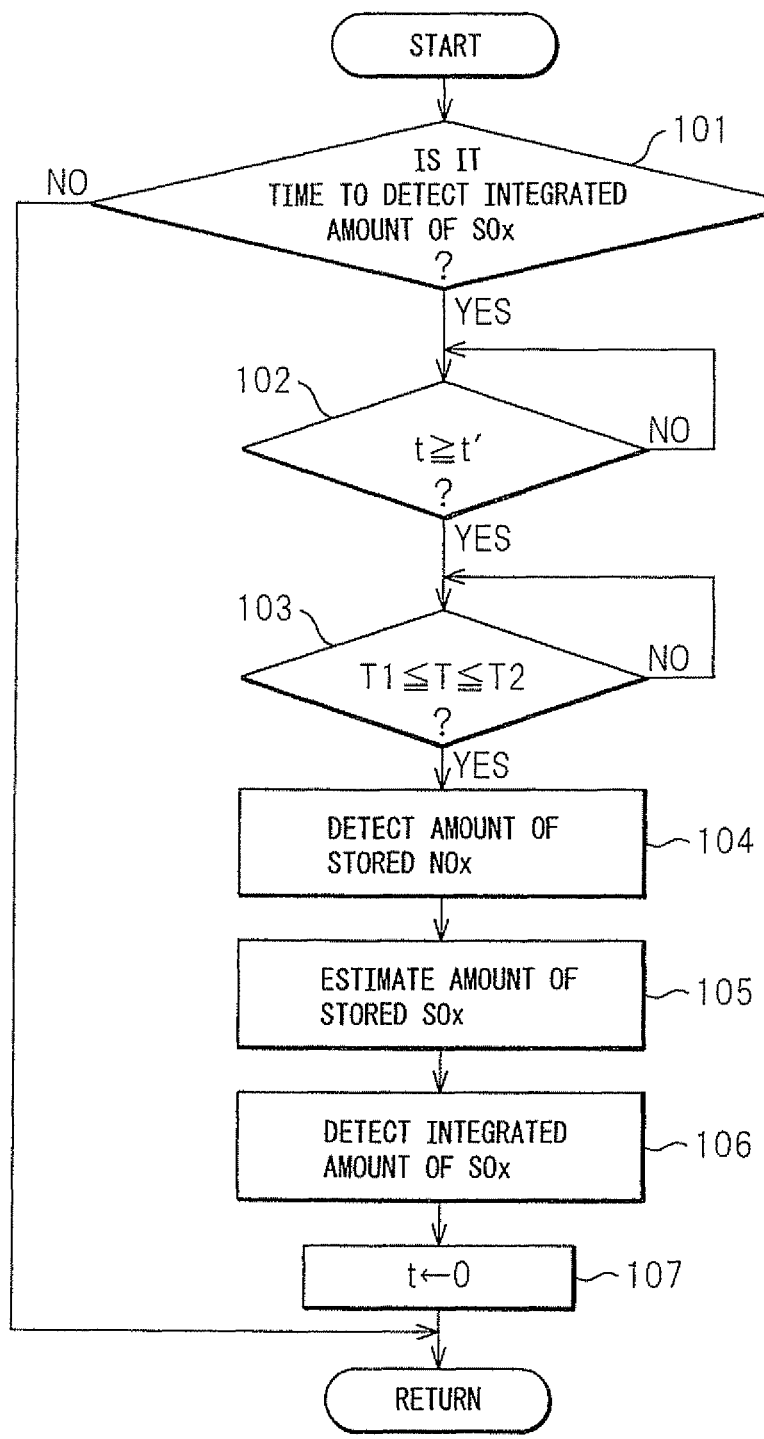
FIG. 3 is a flow chart for detecting an integrated amount of $SO_x$ or a value on the basis of the integrated amount by using of the detector for detecting sulfur components according to the present invention.

FIG. 3 is a flow chart for detecting an integrated amount of $SO_x$ or a value on the basis of the integrated amount by the detector for detecting sulfur components 4 and is carried out in an electronic control unit (not shown). First, at step 101, it is determined if it is a time to detect an integrated amount of $SO_x$. When the result at step 101 is negative, the routine is finished. On the other hand, when it is necessary to detect an integrated amount of $SO_x$ regularly or irregularly, the result at step 101 is positive and the routine goes to step 102.

At step 102, it is determined if an elapsed time (t) which is explained later in detail reaches a set time (t'). This determination is repeated until the result at step 102 is positive. When the result at step 102 is positive, at step 103, a temperature (T) of the storage portion 44 of the detector for detecting sulfur components 4 is measured by the temperature sensor 42 and it is determined if the measured temperature (T) is within a set temperature range from a first temperature (T1) (for example, 350-380 degrees C.) to a second temperature (T2) (for example, 400-430 degrees C.). This determination is repeated until the result at step 103 is positive. In case that a temperature of the exhaust gas is low, when the result at step 101 is negative, for example, the electric heater 43 may be operated such that the result at step 103 is positive. If necessary, the electric heater 43 may be operated such that the temperature (T) of the storage portion 44 is always maintained within the set temperature range (from T1 to T2).

When the result at step 103 is positive, an air-fuel ratio of the exhaust gas in the vicinity of the storage portion 44 is made rich to reduce the oxygen concentration in the vicinity of the storage portion 44. Therefore, $NO_x$ is released from the storage portion 44 and is reduced as follows.

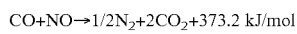

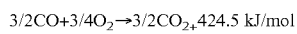

Thus, a quantity of heat of about 490 kJ is produced for 1 mol of $NO_x$. Therefore, an increase value of temperature ΔT (Ta−Tb) between a maximum temperature (Ta) of the storage portion after the air-fuel ratio of the exhaust gas in the vicinity of the storage portion 44 is changed to rich and a temperature (Tb) of the storage portion 44 before the air-fuel ratio of the exhaust gas in the vicinity of the storage portion 44 is changed to rich is measured by the temperature sensor 42. At step 104, an amount of $NO_x$ stored in the storage portion 44 (A) (mol) is detected on the basis of this increase value of temperature ΔT. When it is finished to measure the increase value of temperature ΔT, the air-fuel ratio of the exhaust gas is returned to lean of normal engine operations.

When the amount of stored $NO_x$ (A) is less than the amount of $NO_x$ that can be stored (B) when $SO_x$ is not stored, $SO_x$ is stored in the storage portion 44 and a current amount of stored $SO_x$ (B−A) is estimated at step 105.

A given rate of an amount of $SO_x$ passing through the exhaust passage 1 at the position of the detector for detecting sulfur components 4 is stored in the storage portion 44 of the detector 4. Therefore, at step 106, an integrated amount of $SO_x$ passing through the exhaust passage 1 at the position of the detector 4 during the given period is detected on the basis of the current amount of stored $SO_x$. Next, at step 107, the elapsed time (t) is reset to 0 and the routine is finished.

In the present flow chart, to estimate accurately the amount of $SO_x$ stored in the storage portion 44 (B−A) at step 105, the amount of $NO_x$ stored in the storage portion 44 (A) detected at step 104 must be equal to the current amount of $NO_x$ that can be stored which is decreased by the stored $SO_x$. Namely, when the amount of $SO_x$ stored in the storage portion 44 (B−A) at step 105 is estimated, it is required that the current amount of $NO_x$ that can be stored is stored in the storage portion 44. If the amount of stored $SO_x$ is estimated on the basis of the amount of stored $NO_x$ when the current amount of $NO_x$ that can be stored is not stored in the storage portion, the estimated amount of stored $SO_x$ becomes more than an actual amount.

In the present flow chart, when the elapsed time (t) does not reach the set time (t'), there is some possibility that the current amount of $NO_x$ that can be stored is not stored in the storage portion 44, the result at step 102 is negative so that the processes after step 103 including the estimation of the amount of stored $SO_x$ for detecting the integrated amount of $SO_x$ are prohibited (are not carried out).

The elapsed time (t) is reset to 0 when the engine is started initially or is reset to 0 at step 107 of the present flow chart. In addition to these, the elapsed time (t) is reset to 0 when all amount of $NO_x$ is released from storage portion 44. For example, in the regeneration treatment of the $NO_x$ catalyst device 2, the air-fuel ratio of the exhaust gas is changed to rich and all amount of $NO_x$ is released from the storage portion 44 so that the elapsed time (t) is reset to 0 when the regeneration treatment is finished. On the other hand, to reset the integrated amount of $SO_x$, all amount of stored $SO_x$ is released from the storage portion 44. In this case, all amount of $NO_x$ is also released from the storage portion 44 so that the elapsed time (t) is reset to 0.

Figure 4:
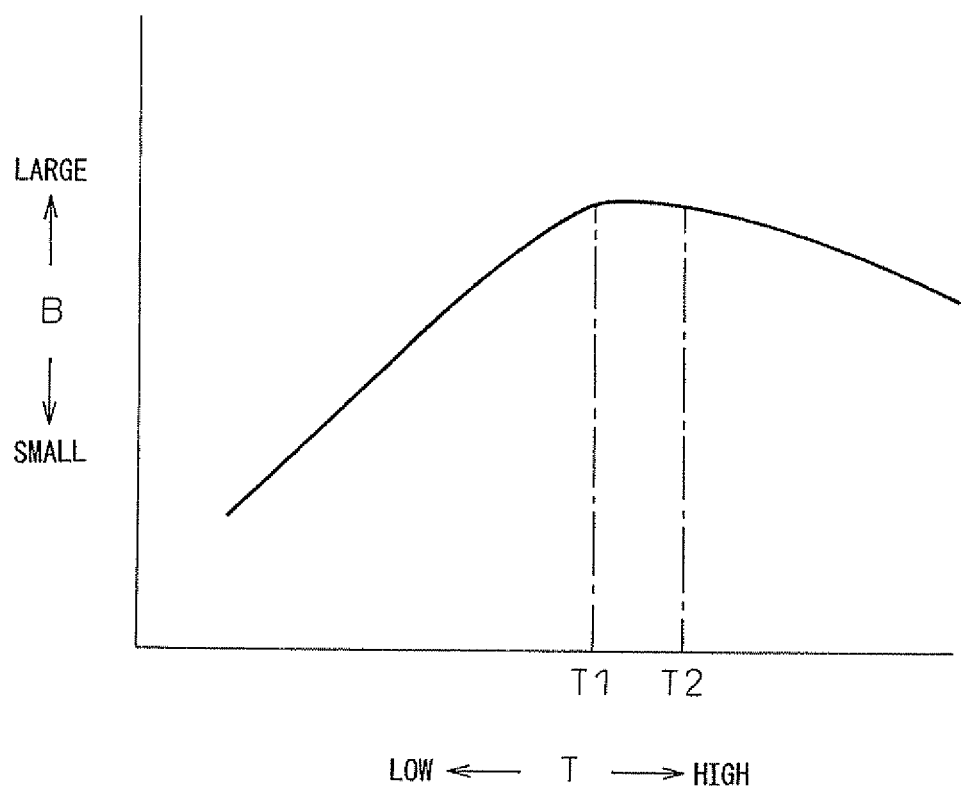
FIG. 4 is a graph showing a relationship between a temperature of the storage portion of the detector for detecting sulfur components according to the present invention and an amount of $NO_x$ that can be stored in the storage portion when $SO_x$ is not stored.

Incidentally, the current amount of $NO_x$ that can be stored in the storage portion 44 is changed in accordance with the temperature of the storage portion 44. As an example, FIG. 4 shows the amount of $NO_x$ that can be stored (B) in the storage portion 44 formed from the $NO_x$ storage material (Ba) when $SO_x$ is not stored. As shown in FIG. 4, the amount of $NO_x$ that can be stored in each amount of stored $SO_x$ is maximum when the temperature of the storage portion 44 is T1 (350-380 degrees C.) and is maintained relative high when the temperature of the storage portion 44 is between T1 and T2 (400-430 degrees C.).

Thus, to accurately estimate the amount of stored $SO_x$ for detecting the integrated amount of $SO_x$, it is preferable that the temperature (T) of the storage portion 44 when the current amount of $NO_x$ stored in the storage portion 44 (A) is detected corresponds with a set temperature of the storage portion 44 at which the amount of $NO_x$ that can be stored (B) when $SO_x$ is not stored is determined as the standard. At least, when the temperature (T) of the storage portion 44 is out of the set temperature range including this set temperature, it is preferable to prohibit the estimation of the amount of stored $SO_x$ for detecting the integrated amount of $SO_x$. For example, when the temperature (T) of the storage portion 44 becomes out of the set temperature range and the amount of $NO_x$ that can be stored decreases by the changing of the temperature of the storage portion 44, if the amount of stored $SO_x$ is estimated on the basis of the amount of stored $NO_x$, the estimated amount of stored $SO_x$ becomes more than the actual amount.

Accordingly, in the present flow chart, when the temperature of the storage portion 44 is out of the set temperature range, the result at step 103 is negative and the processes after step 104 including the estimating of the amount of stored $SO_x$ for detecting the integrated amount of $SO_x$ are prohibited (are not carried out).

The set temperature of the storage portion 44 at which the amount of $NO_x$ that can be stored (B) when $SO_x$ is not stored is determined as the standard is preferably for example 350 degrees C. at which the amount of $NO_x$ that can be stored (B) becomes maximum. The set temperature range at step 103 includes preferably the temperature of the storage portion (for example 350 degrees C.) at which the amount of $NO_x$ that can be stored (B) becomes maximum. Thus, when the amount of stored $SO_x$ for detecting the integrated amount of $SO_x$ or the value on the basis of the integrated amount is estimated, the amount of $NO_x$ stored in the storage portion 44 becomes relatively large so that the amount of stored $NO_x$ can be easily measured.

Incidentally, in case that the storage portion 44 of the detector for detecting sulfur components 4 stores $NO_x$ in the exhaust gas as nitrate, like the present embodiment, if oxygen is supplied in the vicinity of the storage portion 44, NO in the exhaust gas is oxidized to $NO_2$ by the supplied oxygen and is easily stored in the storage portion 44 as nitrate.

In accordance with the engine operating conditions, the oxygen concentration in the exhaust gas flowing into the case 45 becomes relatively low. Therefore, except during the air-fuel ratio of the exhaust gas is intentionally made rich in the regeneration treatment of $NO_x$ catalyst device 2, the process for releasing $NO_x$ from the storage portion 44 mentioned above, or the like, the oxygen pump 46 is preferably operated to supply oxygen in the vicinity of the storage portion 44 such that NO in the exhaust gas is easily stored in the storage portion 44. Particularly, the air-fuel ratio of the exhaust gas in the vicinity of the storage portion 44 is preferably made 40 and over.

Incidentally, the current amount of $NO_x$ that can be stored in the storage portion 44 on the basis of each amount of stored $SO_x$ is gradually decreased according to the deterioration thereof. Therefore, to accurately estimate the amount of stored $SO_x$ for detecting the integrated amount of $SO_x$ or the value on the basis of the integrated amount, the amount of $NO_x$ that can be stored (B) when $SO_x$ is not stored determined as the standard must be updated to a current value. When the current amount of $NO_x$ that can be stored in the storage portion decreases with the deterioration, if the amount of store $SO_x$ is estimated on the basis of the original standard, the estimated amount of stored $SO_x$ becomes more than the actual amount.

Figure 5:
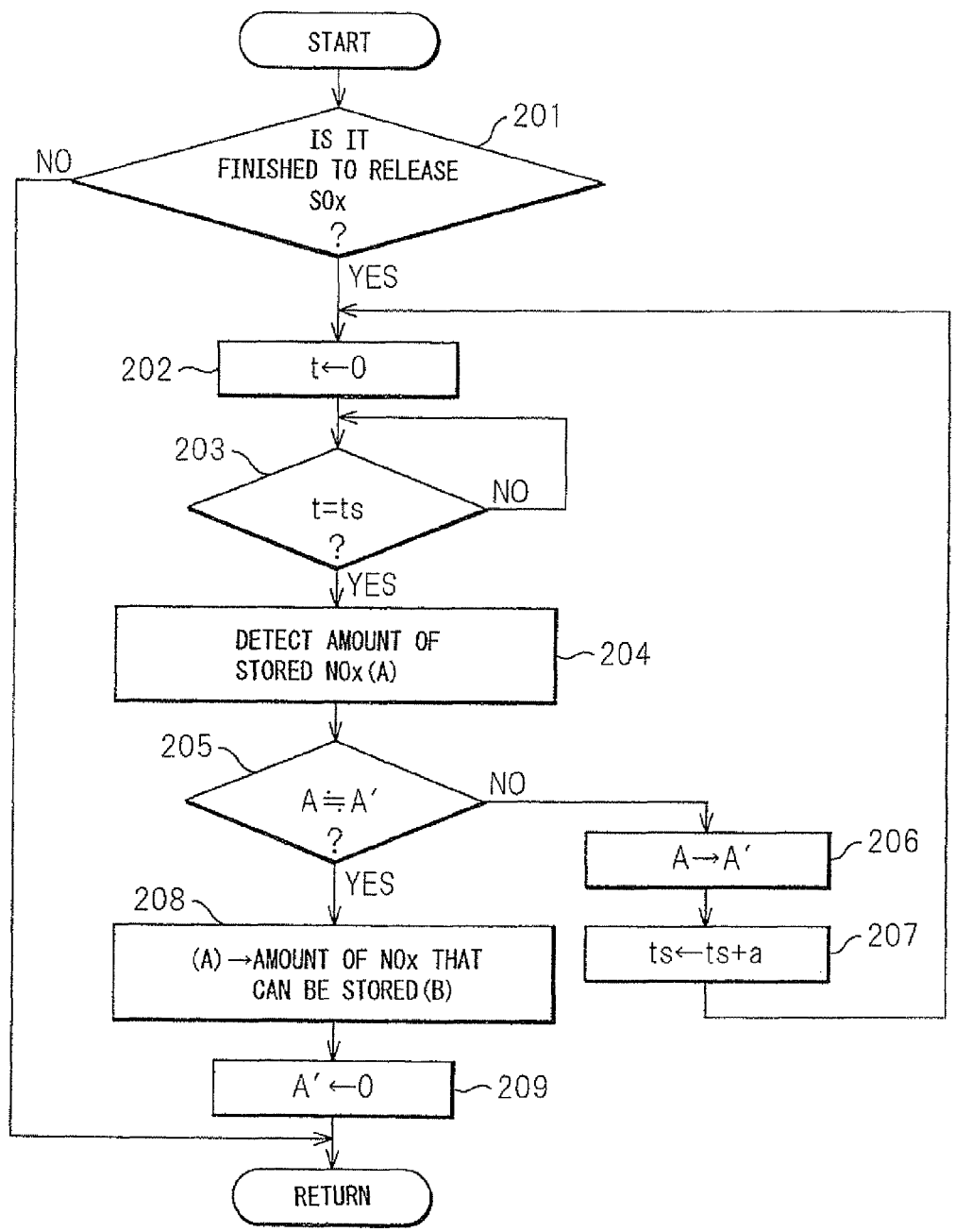
FIG. 5 is a flow chart for updating the amount of $NO_x$ that can be stored in the storage portion when $SO_x$ is not stored of the detector for detecting sulfur components according to the present invention.

FIG. 5 is a flow chart for updating the amount of $NO_x$ that can be stored when $SO_x$ is not stored used as the standard and is carried out in the electronic control unit.

When it is intended to detect an integrated amount of $SO_x$ passing through the exhaust passage 1 at the position of the detector for detecting sulfur compositions 4 during a new given period or a value on the basis of the integrated amount of $SO_x$, the amount of $SO_x$ stored in the storage portion 44 is required to be reset to 0. At step 201, in such a case, it is determined if all amount of $SO_x$ is released from the storage portion 44.

To release $SO_x$ from the storage portion 44, the air-fuel ratio of the exhaust gas must be not only made rich but the temperature of the storage portion 44 must be also made high (for example, 650 degrees C.). Therefore, reduction materials in the exhaust gas may be oxidized by using of the noble metal catalyst on the storage portion 44 to raise the temperature of the storage portion 44 or the electric heater 43 may raise the temperature of the storage portion 44. Thus, when $SO_x$ stored in the storage portion 44 as sulfate is released, of course $NO_x$ stored as nitrate unstable more than sulfate is also released from the storage portion 44.

When the result at step 201 is negative, the routine is finished. On the other hand, when the result at step 201 is positive, at step 202, the elapsed time (t) is reset to 0 as explained in the flow chart in FIG. 3. Next, at step 203, it is determined if the elapsed time (t) reaches a set period (ts). The determination is repeated until the result is positive. When the result at step 203 is positive, at step 204, an amount of $NO_x$ stored in the storage portion 44 (A) during the set period (ts) is detected to make the air-fuel ratio of the exhaust gas rich as mentioned above.

Next, at step 205, it is determined if the amount of stored $NO_x$ detected at this time (A) is equal to about the amount of stored $NO_x$ detected at the last time (A'). At first, the amount of stored $NO_x$ detected at the last time (A') is 0 and thus the result at step 205 is negative. Therefore, the routine goes to step 206.

At step 206, the amount of stored $NO_x$ detected at this time (A) is made the amount of stored $NO_x$ detected at the last time (A'). Next, at step 207, the set period (ts) mentioned above is increased by (a) and the routine returns step 202.

When such processes are repeated, the set period (ts) is gradually lengthened and thus the amount of $NO_x$ stored in the storage portion 44 during the set period (ts) is gradually increased. Finally, the current amount of $NO_x$ that can be stored in the storage portion 44 is stored. Therefore, at next time, the amount of stored $NO_x$ detected at this time (A) is equal to about the amount of stored $NO_x$ detected at the last time (A'), the result at step 205 is positive, and the routine goes to step 208. Thus, the current amount of $NO_x$ that can be stored in the storage portion 44 can be detected accurately at a short time.

The amount of $NO_x$ stored in the storage portion 44 (A) detected in this way is the amount of $NO_x$ that can be stored when the storage portion 44 is exposed only during a short period (a few minutes or a few ten minutes) after all $NO_x$ and $SO_x$ stored in the storage portion 44 have been released and becomes the current amount of $NO_x$ that can be stored in the storage portion 44 (B) when $SO_x$ is not stored because $SO_x$ is not almost stored in the storage portion 44 during such a short period. Accordingly, at step 208, the amount of stored $NO_x$ detected at this time (A) is made the current amount of $NO_x$ that can be stored (B) in the storage portion 44 when $SO_x$ is not stored. Next, at step 209, the amount of stored $NO_x$ detected at the last time (A') is reset to 0 and the routine is finished.

Thus, the current amount of $NO_x$ that can be stored in the storage portion 44 (B) when $SO_x$ is not stored is updated as the standard, and can be used in the estimation of the amount of $SO_x$ stored in the storage portion 44 (B−A) at step 105 of the flow chart in FIG. 3.

In the flow charts of FIGS. 3 and 5, the elapsed time (t) for storing $NO_x$ in the storage portion 44 can be changed to a running distance. The air-fuel ratio of the exhaust gas is made rich to detect the amount of $NO_x$ stored in the storage portion 44 (A). This does not limit to the present invention. For example, even if the oxygen concentration is not dropped, $NO_x$ stored in the storage portion 44 is released when the temperature of the storage portion becomes about 500 degrees C. Accordingly, with utilizing this, the electric heater 43 heats the storage portion 44 and the amount of $NO_x$ stored in the storage portion 44 (A) may be detected on the basis of a quantity of heat used to release all amount of $NO_x$ from the storage portion 44.

When the air-fuel ratio of the exhaust gas is made rich in the regeneration treatment of the $NO_x$ catalyst device 2 and the detection of the amount of $NO_x$ stored in the storage portion 44, the air-fuel ratio of combustion in the engine may be made rich, additional fuel may be supplied into cylinder in exhaust stroke or expansion stroke, or fuel may be supplied to the exhaust gas in the exhaust passage 1.

LIST OF REFERENCE NUMERALS

1: exhaust passage
2: $NO_x$ catalyst device
3: S trap device
4: detector for detecting sulfur components
42: temperature sensor
43: electric heater
44: storage portion

The invention claimed is:

1. A detector for detecting sulfur components, the detector comprising:
 a storage portion configured to store SOx and NOx in the exhaust gas passing through an exhaust passage, in which the more an amount of stored SOx increases, the more an amount of NOx that can be stored decreases; and
 an electronic control unit configured to (i) estimate the amount of stored SOx on the basis of the amount of NOx stored in the storage portion, and (ii) estimate an integrated amount of SOx passing through the exhaust passage during a given period or a value on the basis of the integrated amount,
 wherein the electronic control unit prohibits the estimating of the amount of stored SOx for estimating the integrated amount of SOx or the value on the basis of the integrated amount when a current amount of NOx that can be stored is not stored in the storage portion.

2. The detector according to claim 1, further comprising a temperature sensor that detects a temperature of the storage portion, wherein the electronic control unit prohibits the estimating of the amount of stored SOx for estimating the integrated amount of SOx or the value on the basis of the integrated amount when the temperature of the storage portion is out of a set temperature range.

3. The detector according to claim 2, wherein the set temperature range includes a temperature at which the current amount of NOx that can be stored in the storage portion is maximized.

4. The detector according to claim 1, wherein after all NOx and SOx stored in the storage portion have been released, the electronic control unit estimates the amount of NOx stored in the storage portion during a set period by releasing all the amount of stored NOx, when the set period is gradually lengthened, each amount of NOx stored in the storage portion during each set period is estimated, and a maximum value of the estimated amounts of stored NOx is set as the current amount of NOx that can be stored in the storage portion when SOx is not stored.

5. The detector according to claim 1, further comprising an oxygen pump, wherein the storage portion stores NOx in the exhaust gas as nitrate and oxygen pump supplies oxygen in the vicinity of the storage portion.

6. The detector according to claim 2, further comprising an oxygen pump, wherein the storage portion stores NOx in the exhaust gas as nitrate and the oxygen pump supplies oxygen in the vicinity of the storage portion.

7. The detector according to claim 3, further comprising an oxygen pump, wherein the storage portion stores NOx in exhaust gas as nitrate and the oxygen pump supplies oxygen in the vicinity of the storage portion.

8. The detector according to claim 4, further comprising an oxygen pump, wherein the storage portion stores NOx in the exhaust gas as nitrate and the oxygen pump supplies oxygen in the vicinity of the storage portion.

* * * * *